US009775910B2

(12) United States Patent
Milley et al.

(10) Patent No.: US 9,775,910 B2
(45) Date of Patent: Oct. 3, 2017

(54) STABLE AQUEOUS SUSPENSION

(71) Applicants: Christopher J Milley, Orrville, OH (US); Scott E Peters, Wooster, OH (US)

(72) Inventors: Christopher J Milley, Orrville, OH (US); Scott E Peters, Wooster, OH (US)

(73) Assignee: Ingredient Innovations International, Wooster, OH (US)

( * ) Notice: Subject to any disclaimer, the term of this patent is extended or adjusted under 35 U.S.C. 154(b) by 0 days.

(21) Appl. No.: 14/338,145

(22) Filed: Jul. 22, 2014

(65) Prior Publication Data

US 2014/0328928 A1 Nov. 6, 2014

Related U.S. Application Data

(63) Continuation of application No. 13/848,314, filed on Mar. 21, 2013, now abandoned, which is a continuation of application No. 13/444,557, filed on Apr. 11, 2012, now abandoned, which is a continuation of application No. 11/936,430, filed on Nov. 7, 2007, now abandoned, which is a continuation of application No. 10/678,557, filed on Oct. 3, 2003, now abandoned, which is a continuation of application No. 10/037,573, filed on Jan. 3, 2002, now abandoned.

(51) Int. Cl.

| A61K 36/00 | (2006.01) |
|---|---|
| A61K 47/44 | (2017.01) |
| A61K 35/60 | (2006.01) |
| A61K 36/185 | (2006.01) |
| A61K 36/28 | (2006.01) |
| A61K 36/48 | (2006.01) |
| A61K 36/53 | (2006.01) |
| A61K 36/534 | (2006.01) |
| A61K 36/54 | (2006.01) |
| A61K 36/61 | (2006.01) |
| A61K 36/63 | (2006.01) |
| A61K 36/752 | (2006.01) |
| A61K 9/08 | (2006.01) |
| A61K 31/047 | (2006.01) |
| A61K 31/122 | (2006.01) |
| A61K 31/352 | (2006.01) |
| A61K 31/56 | (2006.01) |
| A23D 7/00 | (2006.01) |
| A61K 31/235 | (2006.01) |
| A61K 31/575 | (2006.01) |
| A61K 38/44 | (2006.01) |
| A61K 47/24 | (2006.01) |
| A61K 47/34 | (2017.01) |
| A61K 47/46 | (2006.01) |

(52) U.S. Cl.
CPC .............. *A61K 47/44* (2013.01); *A23D 7/003* (2013.01); *A61K 9/08* (2013.01); *A61K 31/047* (2013.01); *A61K 31/122* (2013.01); *A61K 31/235* (2013.01); *A61K 31/352* (2013.01); *A61K 31/56* (2013.01); *A61K 31/575* (2013.01); *A61K 35/60* (2013.01); *A61K 36/185* (2013.01); *A61K 36/28* (2013.01); *A61K 36/48* (2013.01); *A61K 36/53* (2013.01); *A61K 36/534* (2013.01); *A61K 36/54* (2013.01); *A61K 36/61* (2013.01); *A61K 36/63* (2013.01); *A61K 36/752* (2013.01); *A61K 38/44* (2013.01); *A61K 47/24* (2013.01); *A61K 47/34* (2013.01); *A61K 47/46* (2013.01); *C12Y 110/02002* (2013.01)

(58) Field of Classification Search
None
See application file for complete search history.

(56) References Cited

U.S. PATENT DOCUMENTS

| 4,170,655 A * | 10/1979 | Zeidler ................... A61K 8/45 512/2 |
| 5,904,932 A * | 5/1999 | De Vringer .......... A61K 8/0241 424/401 |
| 6,294,192 B1 * | 9/2001 | Patel .................... A61K 9/4808 424/450 |
| 6,423,354 B1 * | 7/2002 | Monte ................... A23C 11/04 426/321 |

FOREIGN PATENT DOCUMENTS

| DE | 295761 A5 * | 11/1991 |
| JP | 57042616 A * | 3/1982 |
| JP | H0196109 A * | 4/1989 |

OTHER PUBLICATIONS

Johansson et al, The effect of processing on the content and composition of free sterols and sterol esters in soybean oil. Journal of the American Oil Chemists' Society (1979), 56(10), 886-9.*
Surfactant from Wikipedia, accessed on Oct. 13, 2016, pp. 1-11.*

* cited by examiner

*Primary Examiner* — Qiuwen Mi
(74) *Attorney, Agent, or Firm* — Haug Partners LLP

(57) ABSTRACT

An aqueous suspension of a hydrophobic nutrient is disclosed. In particular, the nutrient, in ester form, is combined with a selected dispersion aid and a dispersion agent(s), and then dispersed in an aqueous medium to form the suspension.

6 Claims, No Drawings

STABLE AQUEOUS SUSPENSION

CROSS REFERENCE TO RELATED APPLICATIONS

This application is a continuation of U.S. application Ser. No. 13/848,314, filed on Mar. 21, 2013, which is a continuation of U.S. application Ser. No. 13/444,557, filed on Apr. 11, 2012, which is a continuation of U.S. application Ser. No. 11/936,430, filed on Nov. 7, 2007, abandoned, which is a continuation of U.S. application Ser. No. 10/678,557, filed on Oct. 3, 2003, abandoned, which is a continuation of U.S. application Ser. No. 10/037,573, abandoned. The contents of these applications are incorporated herein by reference.

BACKGROUND OF THE INVENTION

Field of the Invention

This invention relates to a stable aqueous suspension comprising a nutrient, as well as to a method of rendering a normally hydrophobic nutritional compound or ingredient dispersible in water or in an aqueous system.

Description of the Related Art

Nutritional compounds, i.e. nutritional supplements, have been shown to help prevent the onset of undesirable conditions in man. These substances have been identified as either essential to human health (e.g. vitamins), or may, based on the increasing compilation of studies, play a role in maintaining health. For example, phytosterol and/or phytostanol esters have been shown to reduce serum cholesterol levels in man (mammals) upon consumption, and subsequent digestion in the gut. The mechanism for this is not completely known. Scientists theorize that these compounds block absorption of cholesterol produced and released from the body through the normal hepatic function, or consumed as a component of food. In reducing serum cholesterol levels, current wisdom deduces that heart and circulatory health may be maintained by preventing such conditions as arteriosclerosis, myocardial infarction, etc.

Nutritional ingredients, such as lutein, are currently available in tablets or other dry forms because heretofore they could not be satisfactorily dispersed in water. The nutritional ingredients, such as the phytosterols, phytostanols, lutein, isoflavones, Coenzyme $Q_{10}$, are typically hydrophobic and are not ordinarily dispersible in aqueous systems because they are only slightly water or oil soluble, if to any degree at all.

The nutritional ingredients are desirable for use in beverages and cosmetics, in the form of aqueous suspensions, dispersions, or liposomes. Accordingly, a means for rendering these ingredients water dispersible or dispersible in an aqueous system is needed and desired.

SUMMARY OF THE INVENTION

This invention relates to a stable suspension comprising a nutrient or nutritional ingredient. In particular, the nutrient is in an ester form and is associated with a dispersion aid and a dispersion agent.

DETAILED DESCRIPTION OF THE INVENTION

This invention involves a stable aqueous suspension which comprises a nutrient or a nutritional compound or ingredient.

A suitable nutrient or nutritional ingredient is one which is suitable for therapeutic treatment of an animal, e.g. a human being, by ingestion, e.g. via a beverage, or by topical application, e.g. via a lotion or cream, but which is unfortunately typically insoluble or only slightly soluble in water at room temperature, e.g. 20° C. to 25° C., i.e. it is typically hydrophobic. It is these ingredients which are the subject of this invention. Some suitable nutrients or nutritional ingredients include (1) a compound of the formula,

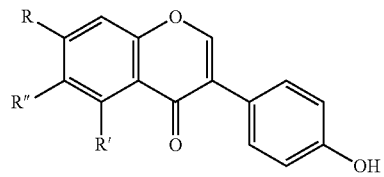

where R is OH, β-glucoside, 6"-O-acetylglucoside, or 6"-O-malonylglucoside; R' is H or OH; and R" is H or $OCH_3$; such as isoflavone, e.g. a soybean derived isoflavone, and a substituted isoflavone, such as daidzein, genistein and glycitein; (2) lutein, (3) a Coenzyme $Q_n$, where n is an integer of 1-12, e.g. Coenzyme $Q_{10}$, (4) a phytosterol, e.g. a stigmasterol, sitosterol, fucosterol, brassicasterol, campesterol, clionasterol, desmosterol, chalinosterol, poriferasterol, (5) a phytostanol, e.g. α or β sitostanol, campestanol, brassicastanol, clionastanol, stigmastanol, desmostanol, chalinostanol, poriferastanol, 22, 23 dihydrobrassicastanol, etc. and (6) a mixture of any of the foregoing ingredients.

For purposes of the dispersions of this invention, which are intended for therapeutic use or as additives in association with a therapeutic treatment of animals, e.g. a human, a particular nutrient or mixture of nutritional ingredients is present in the inventive aqueous dispersions or suspensions in an effective nutritional amount, that is an amount which causes its desired nutritional or therapeutic effect.

The term "amount" as used herein refers to quantity or concentration as appropriate to the context. The amount of nutrient that constitutes a nutritional amount varies according to factors such as potency of the particular ingredient or mixture of ingredients, the mode of administration and the mechanical system used to administer the dispersion. A normally effective amount of a particular nutrient can be selected by those of ordinary skill in the art with due consideration of such factors. Generally, a nutritionally effective amount will be from 0.005 parts by weight to about 25 parts by weight based on 100 parts by weight of the dispersion or suspension.

A suitable aqueous system or medium is selected. A suitable aqueous system or medium for the dispersions or suspensions of this invention include water and an aqueous solution of an organic alcohol of 1 to 6 carbon atoms, e.g. ethanol, propylene glycol, glycerin, etc., and a mixture of the foregoing; present in an amount of up to 10 percent (10%) by weight. The aqueous system is one which will permit a stable dispersion or suspension to be formed therein when combined with the selected nutrient or mixture of nutrients, which in turn is destined to be in the form of at least a mono-ester associated with a suitable dispersion aid. The aqueous system is present in an amount which affords the desired dispersion and is dependent upon the selected nutrient or mixture of nutritional ingredients with the selected dispersion aid. Typically, the aqueous system comprises 55 to 95 weight percent of the dispersion or suspension.

The selected nutrient must first be converted to an ester, e.g. a mono-, di-, tri-ester, etc., if it does not already exist as at least a mono- ester. Such conversion, if required, is conventionally carried out. In this regard, reference is made to such standard text as Briehler, and Pearson, "Survey of Organic Synthesis", Volumes 1 and 2, John Wiley & Sons.

Additionally, reference is made to Ingmar Westar et al., WO 09956558; M. P. van Amerongen et al., EP 00911385 A1 which describes the preparation of stanol, phytosterol and phytostanol esters.

A suitable dispersion aid is selected, i.e. an agent which when combined or associated with the nutrient ester modifies such ester from its crystalline form or morphous form to a dissolved form. The then modified nutrient compound, i.e. ester, can then be further formulated or treated, e.g. pulverized, particularized, homogenized, liquefied, dispersed in oil carrier, whereby it can be easily dispersed in water or an aqueous medium as a suspension.

A suitable dispersion aid includes (1) a triglyceride, such as sunflower oil, soy bean oil, olive oil; a medium chain triglyceride i.e. triglycerides with mixed fatty acids of $C_6$ to $C_{12}$ lengths, such as sn-glyceryl-1-caprylate, -2-caprate, -3-caprylate, etc., and a mixture of any of the foregoing, (2) an essential oil extractive, such as orange oil, lime oil, clove oil, oregano oil, peppermint oil, cinnamon oil, etc., and a mixture of the foregoing; (3) night primrose oil; (4) fish oils; (5) and a mixture of any of the foregoing aids.

The nutrient in ester form is combined or mixed with the dispersion aid, typically at a temperature ranging from 20 to 80° C., e.g. 70-75° C., for 2 to 10 minutes to form the nutrient ester associated with the dispersion aid. By "associate" or "associated" means that the nutrient ester has either reacted with the dispersion aid or has physically interacted with the dispersion aid whereby it is either mixed therewith, encapsulated, wholly or partially, thereby, or becomes part of the interstices thereof, solubilized or diluted.

A suitable dispersion agent is selected from (1) a lecithin, derived from soybean or derived from egg which contain a complex mixture of phospholipids consisting mainly of phosphatidylcholine, phosphatidylethanolamine, phosphatidylinositol, and phosphatidic acid combined with varying amounts of other substances such as triglycerides: the lecithin can be of standard grade or can be modified or refined lecithin e.g. deoiled, hydrogenated, hydroxylated, enzyme modified, acetylated, etc.; (2) a hydrocolloid, e.g. xanthan gum, starch, pectin, gelatin, guar gum, carrageenan, methylcellulose, hydroxypropyl cellulose; (3) a surfactant, e.g. cetylpyridinium chloride, polysorbate 80, sorbitan monostearate, polyglycerol esters, block copolymers of propylene oxide, ethylene oxide; (4) a mixture of any of the forgoing dispersion agents.

An aqueous dispersion of the selected nutrient/aid combination utilizes the dispersion agent in an amount effective to form and stabilize the resultant aqueous dispersion relative to an identical aqueous formulation not containing the dispersion agent, such that the active ingredient does not settle, cream or flocculate after agitation so quickly as to prevent reproducibility, e.g. reproducible dosing. Reproducible application, e.g. dosing, can be achieved if the resultant aqueous suspension is substantially uniform for minimally 1 to 2 hours after agitation thereof. The particular amount of dispersion agent that constitutes an effective amount is dependent upon the particular dispersion agent, the particular aqueous system or medium employed and the particular nutritional ingredient/aid combination, or mixture of ingredients employed. It is therefore not practical to enumerate a specific effective amount for use with specific dispersions or formulations of the invention, but such amount can readily be determined by those of ordinary skill in the art with due consideration of the factors set forth above. Generally, however, the dispersion agent can be present in a formulation in an amount from about 0.01 percent by weight to about 20 percent by weight, more preferably about 0.05 percent to about 10 percent by weight, most preferably 0.5 percent to 5 percent by weight, based on the total weight of the dispersion or formulation.

Typically, the dispersion aid, e.g. sunflower oil, is combined with the active ingredient or nutritional agent, e.g. phytosterol esters, at a temperature of 20° to 80° C. and is mixed for 2 to 10 minutes. Thereafter the combination is added to water containing dispersion agents, and is agitated thereto to form a mixture. The resultant mixture is then subjected to a high shear treatment using any commercially available equipment, e.g. Microfluidics M110, at a shear pressure of 6500 to 24,000 psi, and preferably at a shear pressure of 7000 to 20,000 psi, and most preferably at a shear 10,000 to 12,000 psi, whereby a particle size of the active ingredient typically is less than 500 nm, preferably less than 300 nm, most preferably less than 250 nm, to form the desired aqueous dispersion or suspension.

It is noted that the procedure described above can be modified, namely the order of addition of the nutrient/aid combination, dispersion agent, and aqueous system to form the initial aqueous mixture, i.e. preceding to the described high shear treatment of the mixture.

The resultant aqueous nutrient dispersion can then be further formulated and administered to a patient, e.g. a mammal such as a human being, by any conventional means, such as topically, orally; etc. Typically the dispersion or suspension is combined with other drugs, adjuvants, etc. in the form of a cream or lotion, e.g. a cosmetic, or in the form of a liquid, e.g. a beverage.

EXAMPLES

Example 1

SELIN® brand phytosterol fatty acid esters from Cognis (6.0 g) was dissolved in 24.0 g of NUSUN® oil, from Archer Daniels Midland, a high oleic acid sunflower oil, at 36° C. The resultant solution was added to an aqueous system comprising 78.5 percent by weight of deionized water (157 g), 4.0 percent by weight BLENDMAX K® lecithin from Central Soya (8 g) and 2.5 percent polysorbate 80 (5 g). The resultant mixture was treated two times with a Microfluidizer® M110T from Microfluidics at 8,000 psi shear pressure to obtain a stable dispersion.

Example 2

The procedure of Example 1 was repeated using 15 g of SELIN®, 15 g of NUSUN® oil, 157 g of deionized water, 8 g of BLENDMAX K®, and 5 g of polysorbate 80 to obtain a stable dispersion.

Example 3

SELIN® (6 g) was combined with NUSUN® oil (24 g) and heated at 60° C. for 15 minutes to form a solution. Deionized water (155.8 g) and polysorbate 80 (5 g) were mixed together and heated at 60° C. for 15 minutes and then combined with the solution. BLENDMAX K® lecithin (8 g), citric acid (0.6 g) and potassium sorbate (0.6 g) were added to the combined solution with mixing and then the resultant mixture was passed through a M110T Microfluidizer®, two times at a shear pressure of 8,000 psi. A mean particle size of the stable dispersion of 178.3 nm was obtained.

Example 4

The procedure of Example 3 was repeated with 10 g of SELINO, 20 g of NUSUN® oil, 155.8 g of deionized water, 8 g of BLENDMAX K®, 5 g of polysorbate 80, 0.6 g of citric acid and 0.6 g of potassium sorbate. A mean particle size of 194.6 nm of the stable dispersion was obtained.

Example 5

An experiment was conducted to see how high a percentage of the phytosterol esters could be incorporated into a stable dispersion. The general procedure was to combine BLENDMAX K®, Polysorbate 80, NUSUNO oil and SELIN® and mix these components thoroughly at a temperature of 60°-65° C. To this mix was added deionized water, and the resultant mixture was mixed with a Silverson® high shear mixer. While mixing, citric acid and potassium sorbate were added. Once the mixture became uniform, it was passed twice through a M110T Microfluidizer® at a shear pressure of 8,000 psi. The highest percentage of the SELIN in a stable dispersion obtained was 10.0 percent by weight, using the following weight percentages of the ingredients.

| | |
|---|---|
| Deionized Water | 72.9 |
| BLENDMAX ® | 4.0 |
| Polysorbate 80 | 2.5 |
| NUSUN ® Oil | 10.0 |
| SELIN ® | 10.0 |
| Citric acid | 0.3 |
| Potassium sorbate | 0.3 |

Example 6

The procedure of Example 5 was repeated for lutein esters

| | A (g) | B (g) |
|---|---|---|
| Deionized Water | 72.9 | 67.9 |
| BLENDMAX ® | 4.0 | 4.0 |
| Polysorbate 80 | 2.5 | 2.5 |
| NUSUN ® Oil | 19.8 | 24.75 |
| Citric acid | 0.3 | 0.3 |
| Potassium sorbate | 0.3 | 0.3 |
| Xangold ® Lutein esters | 0.2 | 0.25 |

Stable dispersions were obtained.

Example 7

7.5 g of Xangold®, a 15% lutein ester suspension in vegetable oil from Cognis, was dissolved with 17.5 g of orange oil at 65° C. 4.0 g of BLENDMAX K®, 2.5 g of Polysorbate 80 were added and heated at 65° C. for several minutes. To the heated mixture was added 67.9 g of Deionized water, 0.3 g citric acid, and 0.3 g potassium sorbate while mixing with a Silverson® high shear mixer. The resultant mixture was then passed twice through a M110 Microfluidizer® at a shear pressure of 10,000 psi to yield a stable dispersion.

Example 8

The procedure of Example 7 was repeated using 3.75 g of Xangold® lutein esters and 21.25 g of olive oil instead of orange oil to obtain a stable dispersion.

We claim:
1. A method of rendering a hydrophobic nutritional compound water dispersible, which comprises:
   (a) treating an ester form of the compound with a dispersion aid selected from the group consisting of a triglyceride, an essential oil extractive, night primrose oil, fish oil, and a mixture of any of the foregoing dispersion aids, to form a modified nutrient compound;
   (b) combining a dispersion agent with said modified nutrient compound in an aqueous medium to form an aqueous suspension, wherein said dispersion agent is selected from the group consisting of (a) a lecithin, (b) a surfactant, and (c) a mixture of any of the foregoing dispersion agents, wherein the surfactant is selected from the group consisting of cetylpyridinium chloride, polysorbate 80, sorbitan monostearate, a polyglycerol ester, a block copolymer of propylene oxide, ethylene oxide and a mixture of any of the foregoing surfactants; and
   (c) treating said aqueous suspension to a high shear force to form a stable aqueous suspension.

2. The method as defined in claim 1, wherein said stable suspension has a mean particle size ranging from 50 to 400 nm.

3. The method as defined in claim 1, wherein said ester is an ester of a nutritional compound selected from the group consisting of (a) a phytosterol, selected from the group consisting of stigmasterol, sitosterol, fucosterol, brassicasterol, campesterol, clionasterol, desmosterol, chalinosterol, poriferasterol, and any mixture of the foregoing phytosterols; (b) a phytostanol selected from the group consisting of αsitostanol, βsitostanol, campestanol, brassicastanol, clionastanol, stigmastanol, desmostanol, chalinostanol, poriferastanol, 22, 23 dihydrobrassicastanol, and any mixture of the foregoing phytostanols; (c) lutein, (d) Coenzyme $Q_{10}$, (e) isoflavones, (f) and a mixture of any of the foregoing esters.

4. The method as defined in claim 1, wherein said triglyceride is selected from the group consisting of sunflower oil, soy bean oil, olive oil, a medium chain triglyceride selected from the group containing fatty acids ranging from $C_6$ to $C_{12}$ and a mixture of any of the foregoing triglycerides.

5. The method as defined in claim 1, wherein said essential oil extractive is one selected from the group consisting of orange oil, lime oil, clove oil, oregano oil, peppermint oil, cinnamon oil and a mixture of any of the foregoing extractives.

6. The method as defined in claim 1, wherein said lecithin is selected from the group consisting of a lecithin derived from soybean and a lecithin derived from egg.

* * * * *